United States Patent
Dalal et al.

(10) Patent No.: US 10,695,129 B2
(45) Date of Patent: Jun. 30, 2020

(54) SYSTEM AND METHOD FOR TUMOR ABLATION TREATMENT PLANNING INCLUDING CORE TUMOR, MARGIN AND HEALTHY TISSUE COVERAGE

(71) Applicant: KONINKLIJKE PHILIPS N.V., Eindhoven (NL)

(72) Inventors: Sandeep Dalal, Winchester, MA (US); Jochen Kruecker, Washington, DC (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 196 days.

(21) Appl. No.: 15/552,384

(22) PCT Filed: Mar. 24, 2016

(86) PCT No.: PCT/EP2016/056646
§ 371 (c)(1),
(2) Date: Aug. 21, 2017

(87) PCT Pub. No.: WO2016/151111
PCT Pub. Date: Sep. 29, 2016

(65) Prior Publication Data
US 2018/0042679 A1 Feb. 15, 2018

Related U.S. Application Data

(60) Provisional application No. 62/138,425, filed on Mar. 26, 2015.

(51) Int. Cl.
*A61B 34/10* (2016.01)
*A61B 34/00* (2016.01)
(Continued)

(52) U.S. Cl.
CPC .............. *A61B 34/10* (2016.02); *A61B 18/12* (2013.01); *A61B 18/1477* (2013.01);
(Continued)

(58) Field of Classification Search
CPC ..... A61B 34/10; A61B 34/25; A61B 18/1477; A61B 18/12; A61B 2034/107;
(Continued)

(56) References Cited

U.S. PATENT DOCUMENTS

2009/0326320 A1* 12/2009 Sinofsky .............. A61B 1/0638
600/109
2011/0107270 A1* 5/2011 Wang .................. G06F 19/3481
715/850
(Continued)

FOREIGN PATENT DOCUMENTS

DE        10318204 A1 * 11/2004
WO      2013014648 A1    1/2013

OTHER PUBLICATIONS

Richard Hoppe, Leibel and Phillips Textbook of Radiation Oncology, Third Edition, 1 page (Year: 2004).*

*Primary Examiner* — Ryan Barrett
*Assistant Examiner* — Parmanand D Patel
(74) *Attorney, Agent, or Firm* — Sherry Austin

(57) ABSTRACT

A system for ablation planning and treatment includes a delineation module (124) configured to distinguish tissue types in an image, the tissue types including at least a core tissue and a margin zone encapsulating the core tissue. A treatment planning module (140) is configured to apply weightings in a cost function to prioritize ablation coverage of the tissue types including the core tissue and the margin zone to determine ablation characteristics that achieve an ablation composite in accordance with user preferences. A graphical user interface (122) is rendered on a display to (Continued)

indicate the core tissue, the margin zone, the ablation composite and permit module user selection of one or more treatment methods.

20 Claims, 7 Drawing Sheets

(51) Int. Cl.
| | | |
|---|---|---|
| *A61B 18/14* | (2006.01) | |
| *A61B 18/12* | (2006.01) | |
| *G06F 19/00* | (2018.01) | |
| *A61B 18/00* | (2006.01) | |
| *G06T 7/11* | (2017.01) | |
| *G16H 40/63* | (2018.01) | |
| *G06F 3/0482* | (2013.01) | |
| *G06T 7/00* | (2017.01) | |

(52) U.S. Cl.
CPC .......... *A61B 34/25* (2016.02); *G06F 19/3481* (2013.01); *A61B 2018/00577* (2013.01); *A61B 2018/1425* (2013.01); *A61B 2034/104* (2016.02); *A61B 2034/107* (2016.02); *G06F 3/0482* (2013.01); *G06T 7/0012* (2013.01); *G06T 7/11* (2017.01); *G06T 2207/20104* (2013.01); *G06T 2207/30024* (2013.01); *G06T 2207/30096* (2013.01); *G16H 40/63* (2018.01)

(58) Field of Classification Search
CPC ...... A61B 2034/104; A61B 2018/1425; A61B 2018/00577; G06F 19/3481; G06F 3/0482; G06T 7/0012; G06T 7/11; G06T 2207/30096; G06T 2207/20104; G06T 2207/30024; G16H 40/63

See application file for complete search history.

(56) References Cited

U.S. PATENT DOCUMENTS

| | | |
|---|---|---|
| 2011/0208055 A1 | 8/2011 | Dalai et al. |
| 2012/0277763 A1 | 11/2012 | Greenblatt et al. |
| 2013/0003931 A1* | 1/2013 | Funk .................. A61N 5/1014 378/65 |
| 2014/0058387 A1* | 2/2014 | Kruecker ............ A61B 18/148 606/41 |

* cited by examiner

| Metric | Number of ablations | Max-margins | Logarithmic 10000 | Logarithmic 1000 | Logarithmic 100 | Uniform 10000 | Uniform 1000 | Uniform 100 |
|---|---|---|---|---|---|---|---|---|
| PTV + 5 mm margins maximums | 3<br>4<br>5<br>6 | 76.98%<br>90.15%<br>96.25%<br>99.69% | 79.33%<br>91.08%<br>96.28%<br>98.06% | 80.86%<br>91.08%<br>95.27%<br>96.81% | 80.86%<br>90.62%<br>93.87%<br>95.84% | 82.82%<br>92.66%<br>97.16%<br>99.75% | 82.82%<br>92.66%<br>97.16%<br>99.74% | 82.82%<br>92.66%<br>97.15%<br>99.67% |
| Contiguous margins maximums in mm | 3<br>4<br>5<br>6 | 0<br>2<br>3<br>4 | 0<br>1<br>2<br>3 | 0<br>1<br>2<br>3 | 0<br>1<br>2<br>2 | 0<br>0<br>2<br>3 | 0<br>0<br>2<br>3 | 0<br>0<br>2<br>3 |
| Collateral damage minimums in # voxels | 3<br>4<br>5<br>6 | 967<br>4215<br>13831<br>32316 | 1975<br>5725<br>11349<br>11036 | 2393<br>6577<br>9180<br>7584 | 2813<br>5047<br>5334<br>5058 | 6864<br>15476<br>22856<br>37600 | 6864<br>15476<br>24362<br>35515 | 6864<br>15476<br>22616<br>28033 |

FIG. 5

| FIG. 6-I | FIG. 6-II |
FIG. 6
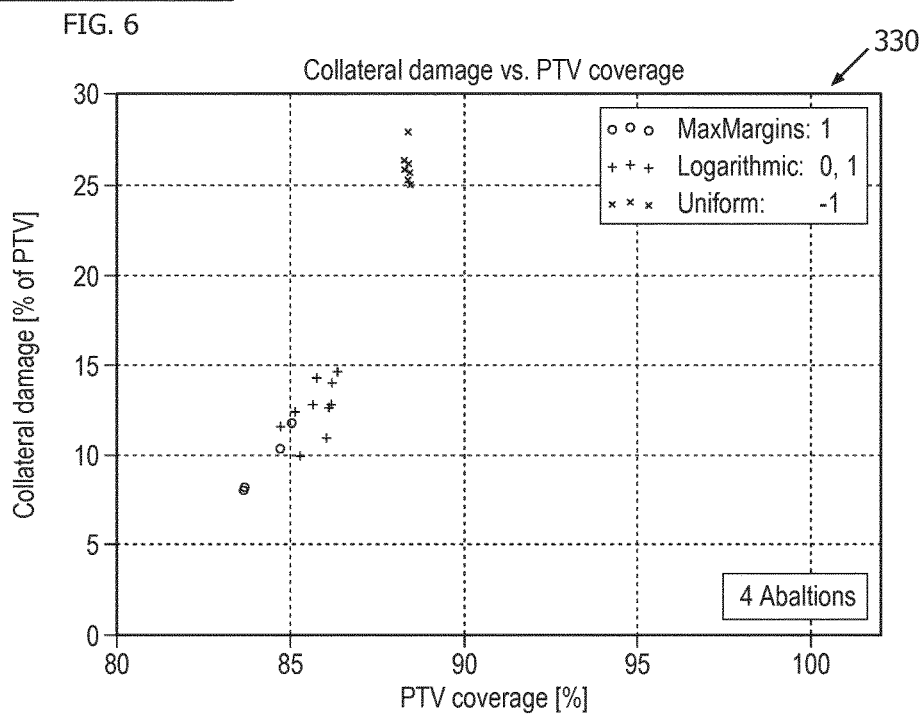
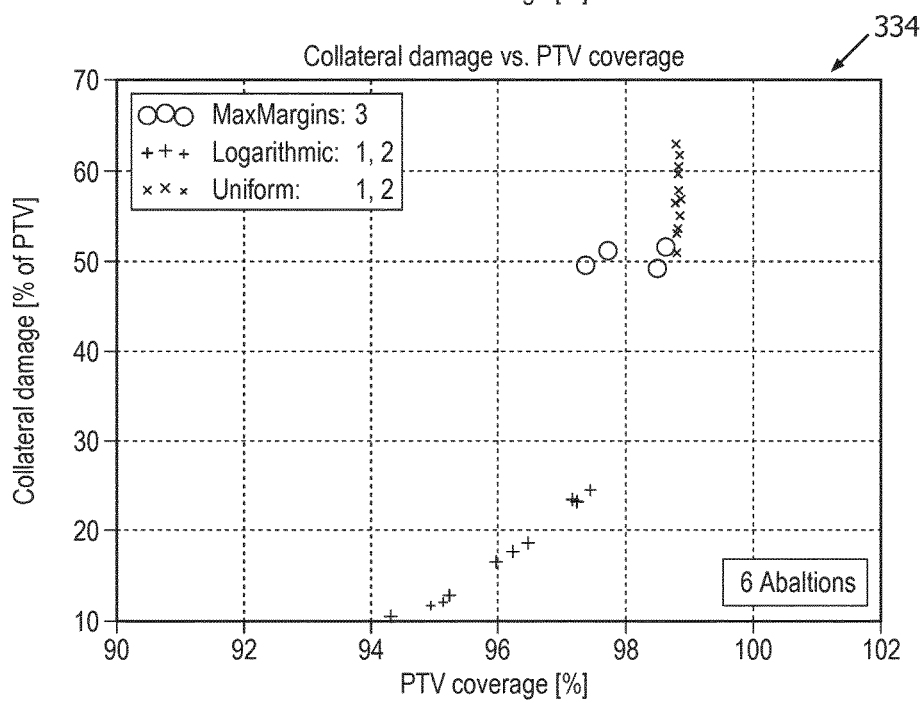
FIG. 6-I

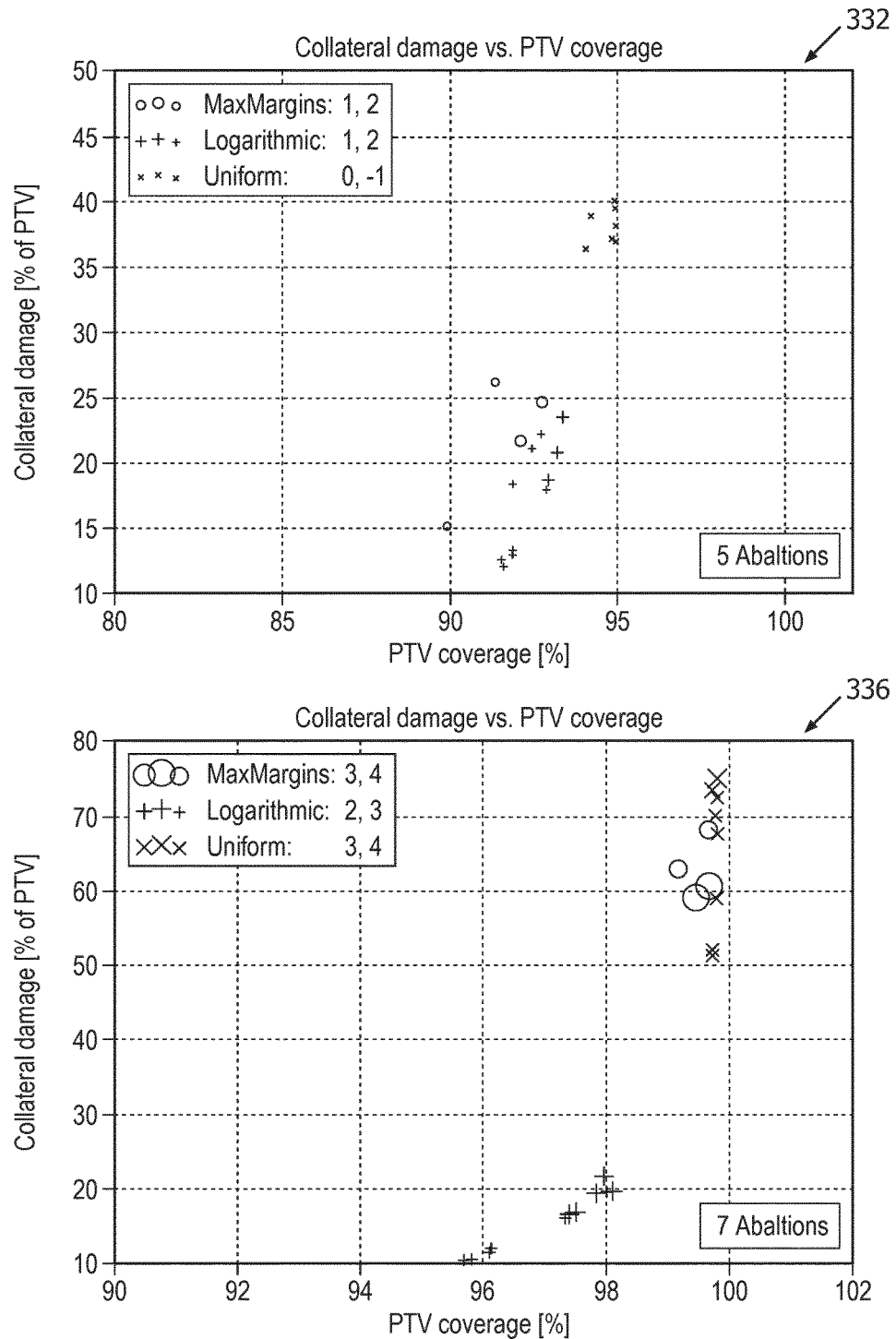
FIG. 6-II

SYSTEM AND METHOD FOR TUMOR ABLATION TREATMENT PLANNING INCLUDING CORE TUMOR, MARGIN AND HEALTHY TISSUE COVERAGE

CROSS-REFERENCE TO PRIOR APPLICATIONS

This application is the U.S. National Phase application under 35 U.S.C. § 371 of International Application Serial No. PCT/EP2016/056646, filed on Mar. 24, 2016, which claims the benefit of U.S. Application Ser. No. 62/138,425, filed on Mar. 26, 2015. These applications are hereby incorporated by reference herein.

BACKGROUND

Technical Field

This disclosure relates to medical instruments and more particularly to an ablation treatment planning system and method that tailors a degree of coverage to a margin region surrounding a tumor where the presence of tumor cells is not apparent from the diagnostic imaging scan used to delineate a core-tumor zone.

Description of the Related Art

Interventional procedures such as radiofrequency ablation (RFA) have been performed as an alternative to more invasive surgical procedures. During RFA, an electrode with an un-insulated tip is inserted into a tumor or lesion to be ablated under imaging guidance. When the electrode is placed, a radiofrequency current is applied to the tip, which creates tissue heating and cell death when tissue temperatures exceed 60° Celsius. In order to destroy tumors that are larger than the volume around the needle tip that is heated and destroyed in a single ablation, the needle tip needs to be repeatedly repositioned with partial overlapping ablation regions to ablate different parts of the tumor. This process needs to be repeated until the entire tumor is "covered" by the set of ablations, also referred to as the "composite ablation." Ablations can also be created by cryoablation, microwave, laser, focused-ultrasound, etc. These are different methods of energy delivery into tissue and each modality of energy delivery has its respective advantages or disadvantages that are known to practitioners.

Interventional procedures for ablation treatment provide benefits for the patient; however, one limitation observed with ablation procedures is the relatively poor outcomes for ablations of large (>3 cm) tumors as compared to surgical resection (excision) of the tumor. This may be attributed to incomplete coverage of larger tumors.

Larger tumors require a larger number of ablations for guaranteeing complete coverage. The clinician usually has imprecise knowledge of how many ablations are needed and uses mental planning methods on where to place ablations with respect to the tumor as seen on the diagnostic imaging scan.

Optimal three-dimensional (3D) positions of all individual ablations are difficult to plan manually/without computer assistance, where "optimal" usually refers to the use of the lowest number of overlapping ablations that maximally covers the tumor and, for a given number of ablations, the precise placement of ablations that destroys the smallest volume of healthy tissue. Another important reason for poor outcomes related to computer-assisted interventions is the lack of accurate placement of ablations during procedure execution.

This issue can be solved by means of intra-procedural instrument localization, e.g., electromagnetic tracked sensors embedded in needles, stylets, introducers, etc. The tumor is delineated using completely manual, semi-automatic or fully automatic segmentation methods on a computer workstation. This delineation is done on diagnostic imaging scans, e.g., computed tomography (CT), positron emission tomography (PET)-CT, magnetic resonance imaging (MRI), etc. Only the core-tumor is delineated as it is distinguishable in the imaging scan.

SUMMARY

In accordance with the present principles, a system for ablation planning and treatment includes a delineation module configured to distinguish tissue types in an image, the tissue types including at least a core tissue and a margin zone encapsulating the core tissue. A treatment planning module is configured to apply weightings in a cost function to prioritize ablation coverage of the tissue types including the core tissue and the margin zone to determine ablation characteristics that achieve an ablation composite in accordance with user preferences. A graphical user interface is rendered on a display to indicate the core tissue, the margin zone, the ablation composite and to permit user selection of a treatment method.

Another system for ablation planning and treatment includes a delineation module configured to distinguish tissue types in an image, the tissue types including at least a core tissue and a margin zone encapsulating the core tissue, the margin zone including a plurality of shells or circumscribing regions outside of the core tissue. A treatment planning module is configured to apply weightings in a cost function to prioritize ablation coverage of the tissue types including the core tissue and the margin zone to determine ablation characteristics that achieve an ablation composite in accordance with user preferences. A graphical user interface is rendered on a display to indicate the core tissue, the margin zone, the ablation composite and permit user selection of one or more treatment methods, wherein the one or more treatment methods include different weightings and are selected on the graphical user interface in accordance with a goal of an ablation treatment plan.

A method for ablation planning and treatment includes delineating tissue types in an image, the tissue types including at least a core tissue and a margin zone encapsulating the core tissue; applying weightings in a cost function to prioritize ablation coverage of the tissue types including the core tissue and the margin zone to determine ablation characteristics that achieve an ablation composite in accordance with user preferences; and rendering a graphical user interface on a display to indicate the core tissue, the margin zone, and the ablation composite.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 5 is a table showing ablation metrics for comparison of ablation methods in accordance with one embodiment;

FIG. 6 depicts graphs showing ablation metrics for comparison of ablation methods in accordance with another embodiment.

DETAILED DESCRIPTION OF EMBODIMENTS

Figure 1:
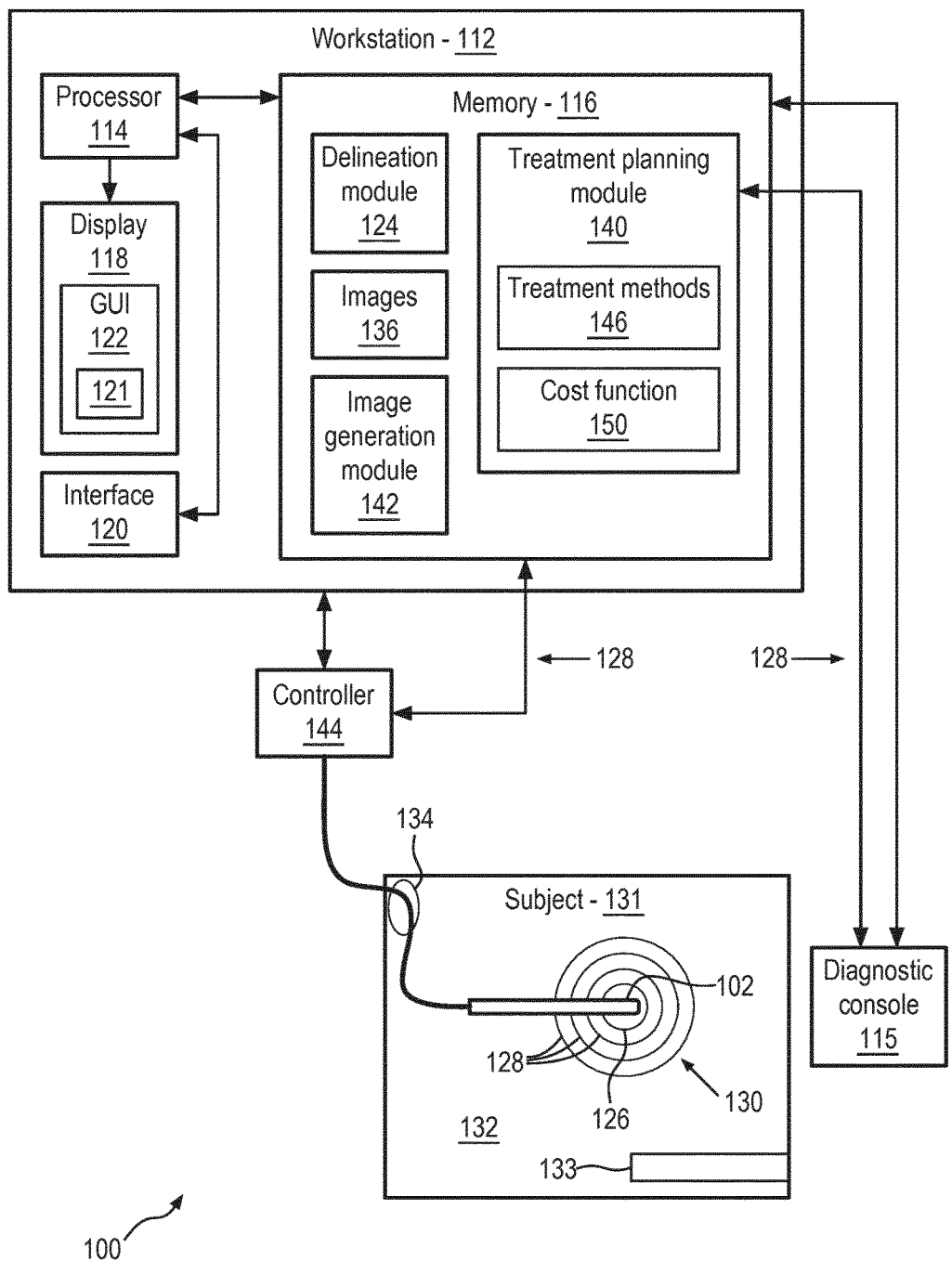
FIG. 1 is a block/flow diagram showing an ablation planning and treatment system which employs a margin zone for evaluating ablation achievement in accordance with one embodiment.

In accordance with the present principles, computer-assisted tumor ablation treatment planning systems are provided that create pre-procedural or intra-procedural treatment plans for minimally-invasive ablation procedures. A treatment plan is optimized to maximally cover a core-tumor region, which can be segmented or delineated on the diagnostic imaging scan, e.g., a CT, PET-CT, MRI 3D volumetric data set, etc. In addition, treatment plans are simultaneously optimized to not cover or minimally cover any critical structures or healthy-tissue that clearly lies outside of the tumor region. Clinicians have different preferences and needs to adapt a treatment plan to an individual patient's needs, focusing, e.g., either on complete coverage of a small core, or on maximizing volumetric coverage beyond the core.

The present principles include a treatment planning system and method that tailors the degree of coverage of an in-between region, e.g., a margin region or zone surrounding the tumor where the presence of tumor cells is not apparent from the diagnostic imaging scan used to delineate the core-tumor zone. Ablation treatment planning methods and user interfaces are provided to tune the coverage of the margin zones to the user's needs.

In addition to the tumor, clinicians may also wish to ablate a margin zone around the core-tumor. The definition of a reasonable margin depends on the clinician, e.g., between a few mm's to 1 centimeter around the tumor. Computer assisted tumor ablation treatment planning systems in accordance with the present principles provide a feature that includes a margin zone within the delineation. The treatment plans generated with such systems reflect coverage of not only the tumor and healthy-tissue as the relevant regions of interest, but also the margin zone or portions of the margin zone.

Treatment planning systems as described herein take into account the margin zone of the tumor explicitly in the computations of an optimized location of ablations by applying a certain priority or weighting to the margin that differs from the core tumor. One goal of this treatment planning system is to maximally or fully cover the core-tumor zone with the requisite number of ablations, and offer a choice of weighting functions to cover the margin zone around the tumor to tune the coverage of the margin based on requirements of the user of the treatment planning system.

The degree to which the priority/weighing associated with the margin zone relative to the core-tumor determines how the ablations are placed in three-dimensional space and affect the treatment plan metrics. This treatment plan includes additional attributes for the treatment plan metrics. The additional attributes reflect coverage of the margin zone. For example, if the margin zone is described as a set of 1 mm thick shells adjacent to the tumor, then the additional attributes would be the percentage of coverage of each shell. As another example, if the margin zone is described as a set of independent spatially distributed regions adjacent to the tumor then the additional attributes would be the percentage of coverage of each region. The treatment plans generated use separate weights to prioritize coverage of the core-tumor zone and each of the margin shell/regions as defined by the user. These weights can be pre-defined as parameters for given planning methods.

It should be understood that the present invention will be described in terms of medical instruments; however, the teachings of the present invention are much broader and are applicable to any planning system or tool where multiple treatment regions are combined. In some embodiments, the present principles are employed in tracking or analyzing complex biological or mechanical systems. In particular, the present principles are applicable to internal tracking or analysis procedures of biological systems including procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIG. 1, a system 100 for ablation treatment planning and progress tracking is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store applications for conducting treatment planning and/or plan execution as the case may be. The workstation 112 performs the treatment planning function and may be a standalone system or be included as part of another system that is used in the ablation procedure, e.g., a diagnostic console associated with an X-ray, MR or CT system, or even embedded within an ultrasound system, for example. A diagnostic console 115 may be part of a separate system or may be connected to the workstation 112 and provide images 136 for ablation planning. The diagnostic console 115 may include, e.g., an X-ray, MR, ultrasound or CT system.

A delineation module 124 provides segmentation/delineation tools that are computer-automated or interactive (with manual supervision) to delineate tissue regions. Segmentation techniques, known in the art may be employed to distinguish tissues in a subject 131 and to identify regions and features within or around the tissues. The tissue regions include core-tumor zone(s) 126, which are the regions of cancerous tissue that are apparent in a diagnostic imaging scan, and a set of margin shells or margin regions 128, which are delineated adjacent to the tumor zone 126. These margin shells or margin regions 128 can be digitally generated and displayed on a display 118. All margin shells together comprise a margin zone 130. Healthy tissue 132 is the tissue region that lies outside of the core-tumor zone 126 and margin-zone 130. Critical structures 133 (e.g., blood vessels, other organs, etc.) are also considered. The set of critical structures 133 (optional) are outside of but in the vicinity of the tumor 126 and margin zones 128. Skin-entry points 134 on the skin surface of the diagnostic imaging scan can be designated. These skin-entry points 134 are marked as entrance locations for ablation needles to access the tumor zone 126 for delivering ablation therapy.

In one embodiment, workstation 112 includes an image generation module 142 configured to generate and display representations of the image regions described above within the volume 131 to be treated. An image 136 within the space or volume 131 can be displayed with region representations shown on the display device 118. Workstation 112 includes the display 118 for viewing internal images of a subject (patient) or volume 131 and may include the image 136 as an overlay or other rendering of the positions of the image regions. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The interface 120 may include the display 118 and a graphical user interface (GUI) 122 to create and visualize margins around the core tumor 126. The display 118 and the GUI 122 may be employed to display and plan quality metrics for individual zones involved in the plan (e.g., core, margins, critical structures). The GUI 122 may include virtual controls 121 to permit a user to select from a choice of several strategies to create plans addressing different clinical needs (e.g., emphasizing one zone over another).

A treatment planning module 140 computes ablation treatment plans. The treatment planning module 140 employs the tissue regions delineated by the delineation module 124. The treatment planning module 140 permits a user to select one or more ablation devices 102 to use in the treatment plan. Ablation needles 102 have an ablation geometry associated therewith (e.g., spherical/ellipsoidal shapes with associated radii depicting ablation size expected when using the device as prescribed by its manufacturer). Other parameters of the ablation needle 102 are controlled by an ablation controller 144, which may be part of the workstation 112 or be a standalone device controlled by the workstation 112. A number of ablations (N) to use in the treatment plan is an input to the treatment planning module 140. The number of ablations can be user-selected or the planning method can compute the necessary number of ablations to maximally (or fully) cover the core-tumor alone (or cover the core-tumor and margin zone together). The treatment planning module 140 includes treatment planning methods or programs 146 that reflect weighting parameters for tissue segmentations for tissue regions. The weighting parameters are employed in computations for both planning and execution. The treatment planning module 140 is triggered, e.g., using virtual controls on the GUI 122 to begin the computation resulting in an ablation plan and metrics.

The treatment planning module 140 produces an ablation plan with metrics reflecting the quantitative attributes of the ablation plan. The metrics for an ablation plan may include, e.g., the percentage of core-tumor covered by the ablation, the percentage of each of the margin shells or regions covered by the ablations, the total volume of healthy tissue destroyed (also called collateral damage), the total volume of critical structures (if included) that are ablated or intersected by the trajectory of the ablation probe when reaching any of the ablation centers from the respective entry point, the selected treatment planning method, a value of an optimized cost function computed for the ablation plan, etc.

The treatment planning module 140 produces an ablation plan with visualization of ablation zones that can show the user how the ablations are precisely placed to cover (or not cover) the various tissue segmentations included in the plan. The individual ablations can be combined into a single region called a composite ablation. The visualization of an ablation plan clearly depicts the spatial relationship between the composite ablation's coverage of the core-tumor 126, the margin zone 130, the healthy tissue 132, critical structures 133 (if included) and skin entry points 134 (if included) as part of the ablation plan.

Figure 2:
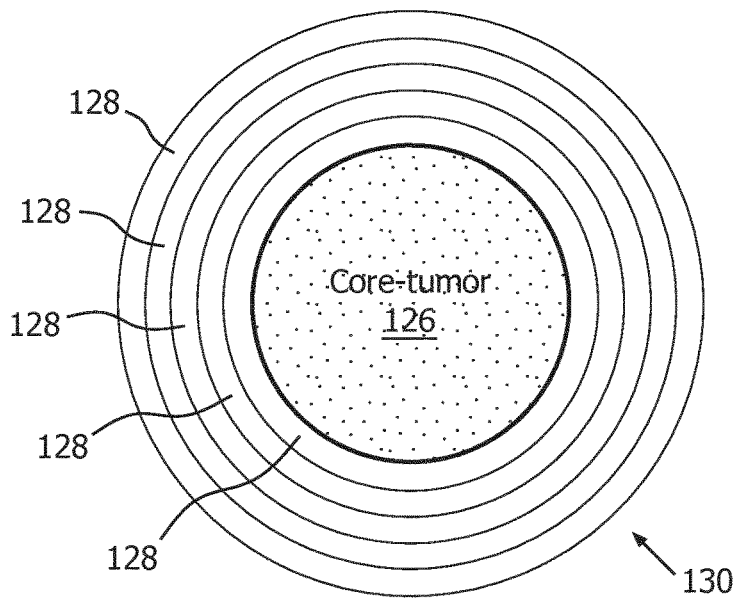
FIG. 2 is a diagram showing core tissue (tumor) and associated margin shells in accordance with one embodiment.

Referring to FIG. 2, a core-tumor 126 is depicted surrounded by a plurality of shells 128 (e.g., 1 mm apart, although any distance may be employed) adjacent to the tumor. The margin shells 128 comprise the margin zone 130. The core-tumor 126 can be distinguished from the margin shells or regions 128 rather than lumping these regions together into one region. Conventional systems lump these regions into a single region called a planned target volume (PTV). A treatment planning system in accordance with the present principles takes into account the margin zone 130 of the tumor explicitly in the calculations of the optimized location of ablations by applying a certain priority/weighting to the margin that differs from the core tumor 126. One goal of the treatment planning system (100, FIG. 1) is to maximally or fully cover the core-tumor zone 126 with a requisite number of ablations, and offer a choice of weighting functions to cover the margin zone 130 around the tumor 126 to tune the coverage of the margin based on requirements of the user.

The degree to which the priority/weighing associated with the margin zone 130 relative to the core-tumor 126 determines how the ablations are placed in three-dimensional space and affect the treatment plan metrics. This treatment plan includes additional attributes for the treatment plan metrics. The additional attributes reflect coverage of the margin zone 130. For example, if the margin zone 130 is described as a set of 1 mm thick shells 128 adjacent to the tumor 126, then the additional attributes would be the percentage of coverage of each shell.

Figure 3:
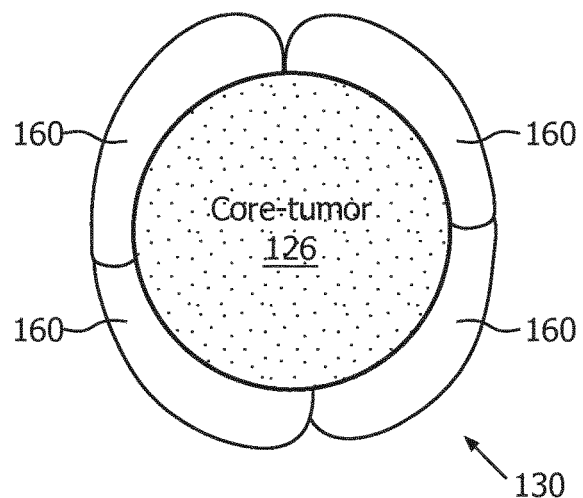
FIG. 3 is a diagram showing core tissue (tumor) and associated margin regions in accordance with another embodiment.

Referring to FIG. 3, in another embodiment, margin regions 160 adjacent to the core-tumor 126 are illustratively shown. The margin regions 160 may be of different sizes along different orientations possibly reflecting greater or lesser certainty in the presence of cancerous cells in each of those regions. The margin regions 160 comprise the margin zone 130. In this example, if the margin zone 130 is described as a set of independent spatially distributed regions (160) adjacent to the tumor 126 then the additional attributes would be, e.g., the percentage of coverage of each region.

Even though FIGS. 2 and 3 depict the regions 128, 160 as two-dimensional; the core-tumor 126, the individual margin shells/regions 128/160, any critical structures or healthy tissue surrounding this region are three-dimensional regions and the treatment planning methods account for the coverage of three-dimensional volumes. FIGS. 2 and 3 demonstrate a simple delineation of margins; however, the present principles are not limited to such margins as there will be additional ways of defining margin zones. The treatment plans generated in accordance with the present embodiments use separate weights to prioritize coverage of the core-tumor zone 126 and each of the margin shell/regions 128/160 as defined by the user. These weights can be pre-defined as parameters for given planning methods.

Referring again to FIG. 1, the treatment planning module 140 makes a plan by placing a target number of ablations, N, over the core-tumor 126, margin zone 130 and healthy tissue 132 and computes a cost function 150 to rank this plan. The different treatment planning methods each have a choice of relative weighting for each of the tissue types that are entered into the cost function 150.

The cost function 150 may be defined as, e.g.:

$$\text{Cost} = W_{ct} * N_{ct} + W_{ht} * N_{ht} + \sum_i (W_{mi} * N_{mi}) + \sum_j (W_{crj} * N_{crj}) \quad \text{(Eq. 1)}$$

In the above cost function (Eq. 1), $W_{ct}$ is the weight for voxels in the core-tumor that are not covered by any of the ablations, $W_{ht}$ is the weight for voxels in the healthy tissue that are covered by any of the ablations, $W_{mi}$ is the weight for voxels in the margin shell or region that are not covered by any of the ablations (i is the index of the margin shell/region, the summation above for i ranges over the complete set of margin shells or regions), and $W_{crj}$ is the weight for voxels in the critical structures that are covered or intersected by trajectories of the ablation device. j is the index of the critical structure, the summation above for j ranges over the complete set of critical structures (if included).

The different voxel counts in the summation include $N_{ct}$=count of voxels in the core-tumor not covered by any of the ablations; $N_{m1}$, $N_{m2}$, etc.=count of voxels in each of the margin shells/regions not covered by any of the ablations; $N_{cr1}$, $N_{cr2}$, etc.=count of voxels in each of the critical structures (if included) that are covered by any of the ablations or intersected by the trajectories of the ablation device from the respective entry points to ablation centers; and $N_{ht}$=count of voxels in the healthy tissue that are covered by any of the ablations.

Without loss of generality, the margin zone 130 is described below as a set of shells that circumscribe the core-tumor 126 and the order of shells is as shown in FIG. 2 (e.g., the 1 mm margin shell 128 being immediately adjacent to the core-tumor 126, and progressively increasing in 1 mm increments to the outermost margin shell 128). Alternatively, the user may choose to use margin regions spatially distributed around the tumor but with different weights for each region (FIG. 3).

The margin regions can be in a pre-defined configuration known to the system, e.g., a set of concentric shells each 1 mm thick that surround the core-tumor to a pre-defined extent, e.g., 5 mm from the boundary of the core-tumor.

Another pre-defined configuration may include a set of concentric shells with pre-defined but non-uniform thickness (e.g., 2 mm for the first shell surrounding the core-tumor, and 1 mm for shells beyond that (to a pre-defined extent). Alternatively, the margin regions can also be in a user-defined configuration wherein the user selects the thickness of each shell and number of shells independently. The pre-defined configuration may also include different radially dependent regions (160) or other configurations.

In accordance with one embodiment, a UNIFORM treatment planning method is described with at least three possible weightings, as listed in Table 1.

TABLE 1

| Tissue zones | Weight | Values | | |
|---|---|---|---|---|
| Unablated tumor core | $W_{ct}$ | 10000 | 1000 | 100 |
| Unablated 1 mm margin shell | $W_{m1}$ | 10000 | 1000 | 100 |
| Unablated 2 mm margin shell | $W_{m2}$ | 10000 | 1000 | 100 |
| Unablated 3 mm margin shell | $W_{m3}$ | 10000 | 1000 | 100 |
| Unablated 4 mm margin shell | $W_{m4}$ | 10000 | 1000 | 100 |
| Unablated 5 mm margin shell | $W_{m5}$ | 10000 | 1000 | 100 |
| Ablated healthy tissue | $W_{ht}$ | 1.0 | 1.0 | 1.0 |

In accordance with another embodiment, a LOGARITHMIC treatment planning method is described with at least three possible weightings, as listed in Table 2.

TABLE 2

| Tissue zones | Weight | Values | | |
|---|---|---|---|---|
| Unablated tumor core | $W_{ct}$ | 10000.0 | 1000.0 | 100.0 |
| Unablated 1 mm margin shell | $W_{m1}$ | 2154.40 | 316.23 | 46.42 |
| Unablated 2 mm margin shell | $W_{m2}$ | 464.16 | 100.0 | 21.54 |
| Unablated 3 mm margin shell | $W_{m3}$ | 100.00 | 31.62 | 10.00 |
| Unablated 4 mm margin shell | $W_{m4}$ | 21.54 | 10.0 | 4.64 |
| Unablated 5 mm margin shell | $W_{m5}$ | 4.64 | 3.16 | 2.15 |
| Ablated healthy tissue | $W_{ht}$ | 1.00 | 1.00 | 1.00 |

In accordance with another embodiment, a MAXMARGINS treatment planning method is described with the weighting as indicated in Table 3. The actual numbers are in scientific format as they reflect a large dynamic range of weights.

TABLE 3

| Tissue zones | Weight | Values |
|---|---|---|
| Unablated tumor core | $W_{ct}$ | 1.0e18 |
| Unablated 1 mm margin shell | $W_{m1}$ | 1.0e15 |
| Unablated 2 mm margin shell | $W_{m2}$ | 1.0e12 |
| Unablated 3 mm margin shell | $W_{m3}$ | 1.0e09 |
| Unablated 4 mm margin shell | $W_{m4}$ | 1,000,000 |
| Unablated 5 mm margin shell | $W_{m5}$ | 1,000 |
| Ablated healthy tissue | $W_{ht}$ | 1.0 |

The numbers in Tables 1-3 should not be construed as limiting as other methods or plans are possible. The user may in fact choose a weighting that resembles the trends shown via the numbers above but is not identical to them. The weighting function may be customized (Custom weighting function).

Note that $W_{cr}$ is not defined in this table, as critical structures are only employed optionally. In case they are used, the value for $W_{cr}$ may be set to a value even higher than the value for $W_{ct}$, the weight for core-tumor coverage that is usually higher than all the other values for the margins or healthy tissue.

Each of these methods has benefits that pertain to achievable tissue coverage. These may include the following. The UNIFORM method has the advantage of maximally covering the entire PTV, i.e., the core-tumor and the margin zone inclusive as compared to the other methods. The LOGARITHMIC method has the advantage of minimally covering healthy tissue as compared to other methods. The MAXMARGINS method has the advantage of covering a larger percentage of the inner core margin shells (that are much more heavily weighted than the other shells) than the other methods. The advantage is gained for margin regions that are heavily weighted compared to other margin regions, similar to the inner margin shells being heavily weighted compared to outer margin shells.

In accordance with one aspect of the present principles, the treatment planning method is selected by the user through an appropriate user-interface (GUI 122). The user-interface 122 would offer a choice of treatment planning methods.

Figure 4:
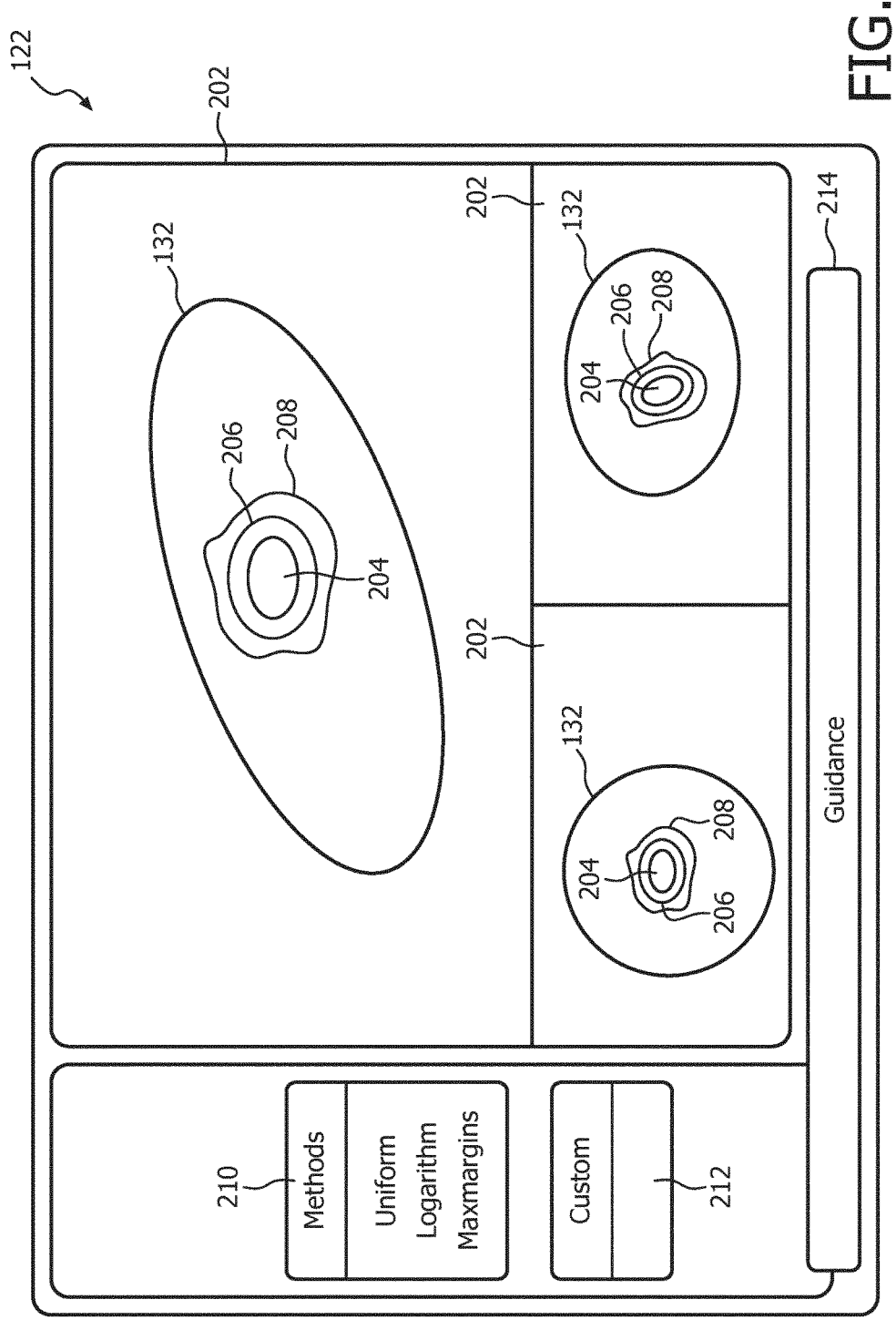
FIG. 4 shows an illustrative graphical user interface showing an image having tissue regions delineated in accordance with an illustrative embodiment.

Referring to FIG. 4, a GUI 122 is shown in accordance with one illustrative embodiment. An ablation plan is computed with the user-selected planning method and is then visualized on the GUI 122 of the workstation 112 (FIG. 1). An example of an ablation plan visualization is shown with an area delineated as a core-tumor 204, a margin zone or region 206 surrounding the core-tumor 204 and a composite ablation region 208 (e.g., composed of multiple individual ablations). The composite ablation region 208 is an output of the treatment planning system. The ablation plan may be monitored visually in real-time to determine when the number of ablations is not sufficient to cover the margin zone 206 or to ensure that the ablation completely covers the core-tumor 204 and the margin zone 206 for that ablation plan.

The GUI 122 includes panes 202 showing views of a region of interest including the tumor 204, the margin region 206 and the ablation treatment region 208. The GUI 122 may include a drop down menu 210 or other control to select a choice of treatment planning method. Names of treatment planning methods to be selected by the user are displayed, e.g., Uniform, Logarithmic, MaxMargins, etc. with associated weight values. The GUI 122 may include a control or input field(s) 212 to make an explicit choice of a Custom treatment planning method that implies a user enters a set of weights for each of the zones.

The GUI 122 may include a guidance control window 214 configured to provide guidance to the user for selecting a treatment planning method. For example, a clinically relevant statement may be offered by the system to the user implicitly enabling the selection of the planning methods. For example, a user may select the method or have a cursor hover over the name of the method. The guidance window 214 may highlight advantages to the weighting of the method. In an alternate embodiment, a user may select a statement that supports the treatment plan goals. For example, "I want to minimize the collateral damage with higher priority" implies the automatic selection of the Logarithmic method; if the user indicates "I want to maximize the coverage of the margin zone with higher priority" implies the automatic selection of the MaxMargins method, or if the user indicates "I want to maximize coverage of the PTV without any preference for the core-tumor relative to the margins" implies the automatic selection of the Uniform method.

In another embodiment, the treatment plan can run more than one treatment planning method with different weighting sets for a given tumor. A "pre-specified configuration of treatment plans" may be automatically run or run with the user's confirmation to permit results of the various plans to be compared, e.g., in a tabular or other visual presentation form. For example, the system 100 (FIG. 1) would automatically run ablation treatment plans with all or some of the methods with selected parameter sets (the weighting values). The user-interface 120 (FIG. 1) would then show to the user the computed ablation plans with the achieved metrics for each of the methods with those parameter sets. The presentation of the metrics could be in tabular form with color coding, etc. to assist the user in detecting the best performing method versus, the next best performing method for a given metric as illustratively depicted in FIG. 5.

Referring to FIG. 5, a table 300 illustratively shows a comparison of metrics for different treatment planning methods (e.g., MaxMargins, Logarithmic and Uniform). The numbers 10000, 1000, 100 at a top of columns 304 of the table reflect the weight of the core-tumor for that selected method. Shaded portions 306 highlighted in any cell 302 represents the method that achieved the best (respectively, second-best, third-best, etc.) performance for one of the metrics (listed in metric column 310) for that number of ablations in a respective row 312. The best, second-best, etc. may be indicated by different colors, shadings, etc.

The presentation could also be in graphical form as illustratively depicted in FIG. 6 such that the user would be able to judge at a glance the relative performance of the methods, and the user may select one of the ablation plans presented to continue further with treatment procedure execution.

Referring to FIG. 6, four graphs 330, 332, 334 and 336 provide a graphical comparison of two metrics Collateral Damage versus PTV Coverage achieved with the different treatment planning methods (e.g., MaxMargins, Logarithmic, Uniform). The size of circle in each graph 330, 332, 334 and 336 represents the size of the contiguous margin achieved by that method—larger circles indicate higher contiguous margins. Other presentation methods and comparisons may also be employed.

As described, the present principles provide for a visual presentation of tissue elements in the graphical user interface such as the margin zone definition that is explicitly delineated outside of the core-tumor either through margin shells circumscribing the tumor or regions around the tumor. The visual presentation of ablation plans is shown with coverage of margin zones explicitly identified in visualization of coverage of composite ablation and margins on top of the core-tumor or PTV. Treatment planning methods are explicitly or implicitly selected by the user. The output of tabular/numeric presentation of margin zone coverage of individual shells or regions is also provided. Numerical/visual presentation of ablation plan metrics for different treatment planning methods leading to selection of a preferred treatment planning method by the user is also provided.

Figure 7:
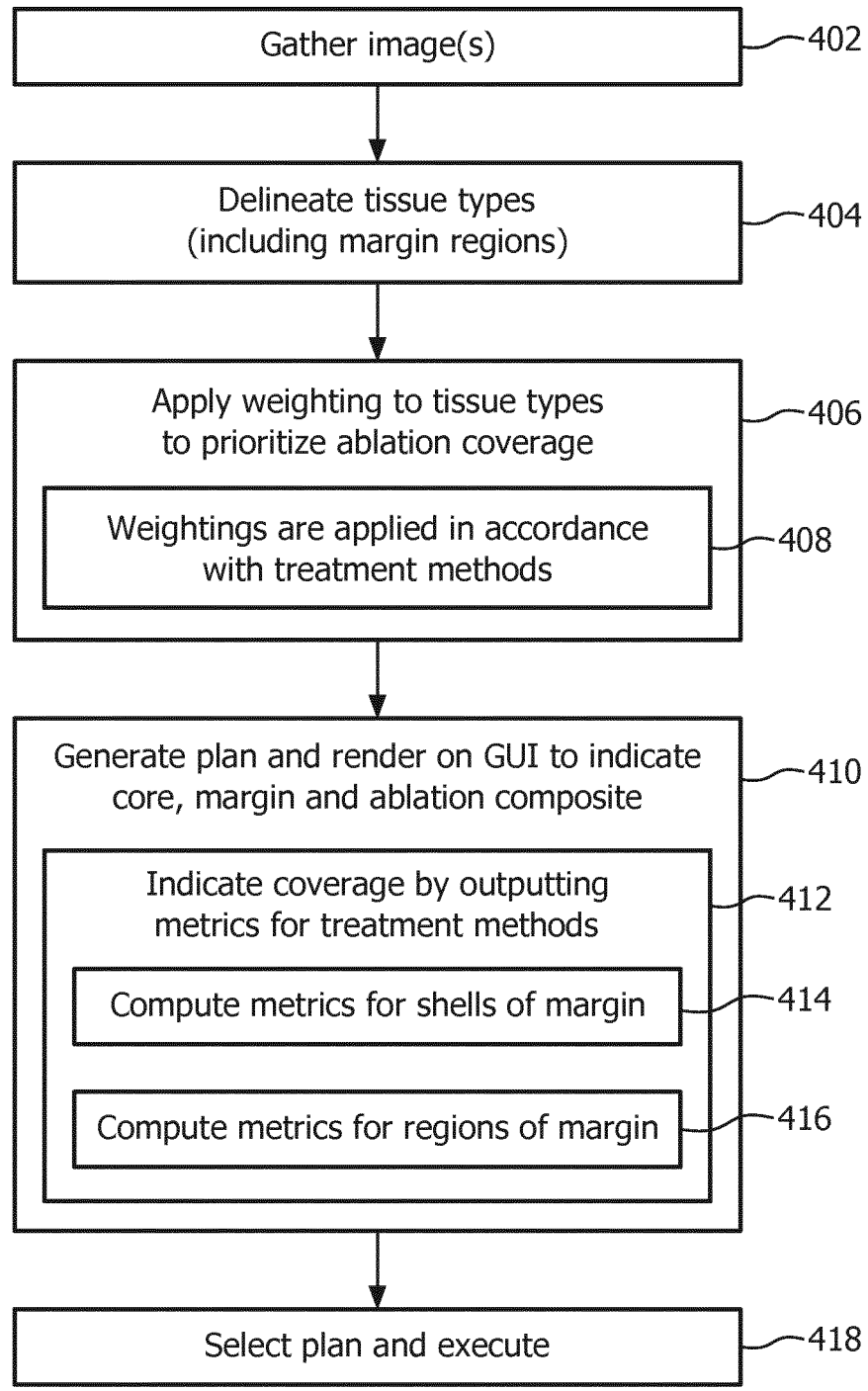
FIG. 7 is a flow diagram showing a method for ablation planning and treatment in accordance with illustrative embodiments.

Referring to FIG. 7, a method for ablation planning and treatment is illustratively shown in accordance with the exemplary embodiments. In block 402, an image or images are gathered for planning an ablation procedure. In block 404, tissue types are delineated or segmented in the image. The tissue types include at least a core tissue and a margin zone encapsulating the core tissue. Other tissue types may include healthy tissue surrounding the core tissue, skin access points and critical structures.

In block 406, weightings are applied in a cost function to prioritize ablation coverage of the tissue types including the core tissue and the margin zone to determine ablation characteristics that achieve an ablation composite in accordance with user preferences. The weighting may be influenced by a number of factors including the tissue types, the type of ablation device to be used in the treatment plan, the number of ablations (N) to use in the treatment plan, the treatment planning method that best reflects the user's desired approach. The cost function is employed to minimize the amount of ablation, and through the weighting, optimize/minimize the amount of collateral damage (damage to healthy tissue), the percentage coverage of the margin zone, the percentage coverage of the core tissue, etc.

In block 408, the weightings are provided using selectable treatment methods. The selectable treatment methods may be selected by a user using the graphical user interface, which includes a selection control. The selection control permits the user to select one or more treatment methods. Each treatment method has a different approach to the ablation and provides information to the user to assist in the appropriate selection. The one or more treatment methods include different weightings for the cost function. The different weightings are determined in accordance with a goal of the ablation treatment plan. The one or more treatment methods may include at least one of a uniform treatment plan, a logarithmic treatment plan, a maxmargin treatment plan and a custom treatment plan.

In block 410, a plan is generated and rendered on a graphical user interface on a display to indicate the core tissue, the margin zone, and the ablation composite. In block 412, coverage of the margin zone is indicated using metrics presented in one or more of a table, a graph or a number for determining the coverage for a planned ablation procedure in accordance with each of a plurality of treatment methods. The treatment planning system produces an ablation plan with metrics reflecting the quantitative attributes of the ablation plan. The metrics for an ablation plan may include the percentage of core-tumor covered by the ablations, the percentage of each of the margin shells or regions covered by the ablations, the total volume of healthy tissue destroyed (also called collateral damage), the total volume of critical structures (if included) that are ablated or intersected by the trajectory of the ablation probe when reaching any of the ablation centers from the respective entry point, the number of ablations in a selected treatment planning method, the value of the optimized cost function computed for the ablation plan, etc.

The metrics may be employed to compare treatment approaches and to evaluate plans in terms of overall goals. The margin zone may include a plurality of shells, each shell being spaced apart from one another and existing outside of the core tissue. In block 414, the ablation coverage metrics may be computed within each shell of the margin zone. The margin zone may include a plurality of regions adjacent to and surrounding the core tissue, each region existing outside of the core tissue. In block 416, ablation coverage metrics may be computed within each region of the margin zone.

In block 418, the best plan is selected (minimized cost, best coverage of margin zone, etc.) and the plan is executed to treat a patient.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for tumor ablation treatment planning including core tumor, margin and healthy tissue coverage (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for ablation planning and treatment, comprising:
 a delineation module configured to distinguish tissue types in an image, the tissue types including at least a core tissue and a margin zone encapsulating the core tissue;
 a treatment planning module configured to apply each of at least two sets of weightings in a cost function to prioritize ablation coverage in and surrounding a planned treatment volume including the core tissue and in the margin zone to determine candidate treatment plan to achieve an ablation composite in accordance with user preferences; and
 a graphical user interface rendered on a display to indicate the core tissue, the margin zone, the ablation composite and permit user selection of one or more treatment method, the graphic user interface including a graphic representation representing a portion of the region covered by the ablation relative to collateral damage comprising a volume of the healthy tissue destroyed by ablation.

2. The system as recited in claim 1, wherein the margin zone includes at least two discretely delineated shells, each shell being spaced apart from others and existing between the core tissue and healthy tissue.

3. The system as recited in claim 2, wherein the treatment planning module is configured to selectively apply one of a plurality of predefined treatment methods, each pre-defined treatment planning method including a method with preassigned weighting for each of the shells.

4. The system as recited in claim 1, wherein the margin zone includes a plurality of regions adjacent to and surrounding the core tissue, the regions being independently spatially distributed peripherally around the core tissue.

5. The system as recited in claim 1, wherein the tissue types further include healthy tissue surrounding the core tissue and critical structures.

6. The system as recited in claim 3, wherein the plurality of treatment planning methods implement at least one of a uniform treatment plan, a logarithmic treatment plan and a maxmargin treatment plan.

7. The system as recited in claim 1, wherein the treatment planning module is configured to selectively apply one of a plurality of predefined treatment methods, the plurality of treatment planning methods including different weightings for each of a plurality of regions of the margin zone, the weighting being selected in accordance with a goal of the ablation treatment plan.

8. The system as recited in claim 7, wherein coverage of the margin zone is indicated in metrics, for each of the treatment planning methods, presented on the display of the graphical user interface in one or more of a table, a graph or a number for determining the coverage for each of the treatment planning methods.

9. The system as recited in claim 3, wherein the plurality of treatment planning methods includes a custom treatment plan.

10. The system as recited in claim 1, wherein
 the margin zone includes a plurality of shells circumscribing the core tissue;
 the treatment planning module is configured to apply one or more treatment methods; and wherein the one or more treatment methods include different weightings for each of the shells and the weightings are selected on the graphical user interface in accordance with a goal of an ablation treatment plan.

11. The system as recited in claim 10, wherein the plurality of shells include an automatically selectable predefined configuration or a user-provided configuration.

12. The system as recited in claim 10, wherein the tissue types further include healthy tissue surrounding the core tissue and critical structures.

13. The system as recited in claim 10, wherein the treatment planning module simulates at least one of a uniform treatment plan, a logarithmic treatment plan and a maxmargin treatment plan.

14. The system as recited in claim 10, wherein coverage of the margin zone is indicated on the display of the user interface in metrics, for one or more treatment methods, presented in one or more of a table, a graph, or a number for determining the coverage for a planned ablation procedure.

15. A method for ablation planning and treatment, comprising:
 delineating at least a core tissue and a margin zone encapsulating the core tissue of a diagnostic imaging scan, the margin zone including a plurality of regions, wherein the core tissue is a tumor and tumor cells in the margin region are not apparent from the diagnostic imaging scan;
 applying weightings in a cost function to prioritize ablation coverage including applying different weightings to the core tissue and the plurality of regions of the margin zone to determine ablation characteristics that achieve an ablation composite in accordance with user preferences; and
 rendering a graphical user interface on a display to indicate ablation coverage in the core tissue and in each of the plurality of regions of the margin zone, in the ablation composite, the graphic user interface including a graphic representation representing a percentage of the core region covered by the ablation relative to collateral damage, the collateral damage comprising a volume of the healthy tissue destroyed by ablation.

16. A system for ablation planning and treatment, comprising:
 a user interface including a user input device and a display;
 one or more processors interconnected with the user interface and configured to:
  receive a diagnostic image of a patient,
  with input from the user input device, segment the received image to identify a core region including tumor tissue and at least a first margin region and a second margin region surrounding the core tissue, applying weightings to a cost function to optimize ablation coverage to the core region, the first margin region, the second margin region, and healthy tissue surrounding the core region and the first and second margin regions, receiving and applying each of a plurality of ablation treatment algorithms, each treatment algorithm having different weightings for the cost function, applying each of the treatment algorithms to the segmented image to determine ablation coverage in each of the core region, the first margin region, the second margin region, and the healthy tissue, generating a display indicative of ablation metrics reflecting quantitative attributes of each of the treatment algorithms, the quantitative attributes including ablation coverage of each of the core region, the first margin region, the second margin region, and the healthy tissue, the display including a graphic representation representing a completeness of coverage of the core region covered by the ablation relative to collateral damage, the collateral damage comprising a volume of the healthy tissue destroyed by ablation, receiving a selection of one of the ablation planning algorithms from the user input device, and controlling an ablation device to perform ablation in the imaged region of the subject in accordance with the selected ablation treatment plan.

17. The system as recited in claim 16, wherein the cost function maximizes ablated voxels in the core region, minimizes ablated voxels in the healthy region, and optimizes ablated voxels individually in each of the margin regions.

18. The system as recited in claim 16, wherein the cost function is defined as:

$$\text{Cost} = W_{ct} * N_{ct} + W_{ht} * N_{ht} + \sum_{i}(W_{mi} * N_{mi}) + \sum_{j}(W_{crj} * N_{crj}),$$

where
- $W_{ct}$ is the weight of voxels in the core region not covered by the ablations,
- $W_{ht}$ is the weight for the voxels in the healthy tissue that are covered by the ablations,
- $W_{mi}$ is the weight for voxels in an $i^{th}$-margin region not covered by the ablations,
- $W_{crj}$ is the weight for voxels in critical structures that are not covered or intersected by trajectories of the ablation device, where j is an index of critical structures,
- $N_{ct}$ is a count of the voxels in the core region not covered by the ablations,
- $N_{mi}$ is a count of voxels in each of the margin regions not covered by ablations,
- $N_{crj}$ is a count of the voxels in each of the critical structures, if any, that are covered by the ablations or intersected by trajectories of the ablation device, and
- $N_{ht}$ is a count of the voxels in the healthy tissue covered by the ablations.

19. The system as recited in claim 16, wherein the treatment algorithms include a uniform treatment planning algorithm, a logarithmic treatment planning algorithm, and a maxmargins treatment planning algorithm.

20. The system as recited in claim 19, wherein the weights of the uniform treatment planning algorithms include:

| Tissue zones | Weight | Values | | |
|---|---|---|---|---|
| Unablated tumor core | $W_{ct}$ | 10000 | 1000 | 100 |
| Unablated 1 mm margin shell | $W_{m1}$ | 10000 | 1000 | 100 |
| Unablated 2 mm margin shell | $W_{m2}$ | 10000 | 1000 | 100 |
| Unablated 3 mm margin shell | $W_{m3}$ | 10000 | 1000 | 100 |
| Unablated 4 mm margin shell | $W_{m4}$ | 10000 | 1000 | 100 |
| Unablated 5 mm margin shell | $W_{m5}$ | 10000 | 1000 | 100 |
| Ablated healthy tissue | $W_{ht}$ | 1.0 | 1.0 | 1.0, | the weightings of the logarithmic treatment planning algorithm include:

| Tissue zones | Weight | Values | | |
|---|---|---|---|---|
| Unablated tumor core | $W_{ct}$ | 10000.0 | 1000.0 | 100.0 |
| Unablated 1 mm margin shell | $W_{m1}$ | 2154.40 | 316.23 | 46.42 |
| Unablated 2 mm margin shell | $W_{m2}$ | 464.16 | 100.0 | 21.54 |
| Unablated 3 mm margin shell | $W_{m3}$ | 100.00 | 31.62 | 10.00 |
| Unablated 4 mm margin shell | $W_{m4}$ | 21.54 | 10.0 | 4.64 |
| Unablated 5 mm margin shell | $W_{m5}$ | 4.64 | 3.16 | 2.15 |
| Ablated healthy tissue | $W_{ht}$ | 1.00 | 1.00 | 1.00, | and
the weightings of the maxmargin treatment planning algorithm are:

| Tissue zones | Weight | Values |
|---|---|---|
| Unablated tumor core | $W_{ct}$ | 1.0e18 |
| Unablated 1 mm margin shell | $W_{m1}$ | 1.0e15 |
| Unablated 2 mm margin shell | $W_{m2}$ | 1.0e12 |
| Unablated 3 mm margin shell | $W_{m3}$ | 1.0e09 |
| Unablated 4 mm margin shell | $W_{m4}$ | 1,000,000 |
| Unablated 5 mm margin shell | $W_{m5}$ | 1,000 |
| Ablated healthy tissue | $W_{ht}$ | 1.0. |

* * * * *